United States Patent [19]

Saffran et al.

[11] Patent Number: 4,868,311
[45] Date of Patent: Sep. 19, 1989

[54] BIOTINYLATED PSORALENS

[75] Inventors: Wilma A. Saffran, Forest Hills, N.Y.; Richard L. Edelson, Westport; Francis P. Gasparro, Hamden, both of Conn.; John T. Welsh; Charles R. Cantor, both of New York, N.Y.

[73] Assignee: The Trustees of Columbia University in the City of New York, New York, N.Y.

[21] Appl. No.: 847,422

[22] Filed: Apr. 2, 1988

[51] Int. Cl.$^4$ ............................................. C07D 519/00
[52] U.S. Cl. ....................................... 548/303; 436/92
[58] Field of Search ........................... 548/303; 436/92

[56] References Cited

U.S. PATENT DOCUMENTS 4,582,789 4/1986 Sheldon et al. ........................ 435/6

OTHER PUBLICATIONS

Pierce Chemical Co., 1986–1987 Handbook, p. 305.

W. Saffran et al., *Proc. Natl. Acad. Sci., USA*, 79: 4594–4578 (1982).

*Primary Examiner*—Richard A. Schwartz
*Attorney, Agent, or Firm*—John P. White

[57] ABSTRACT

The present invention provides a compound having the formula

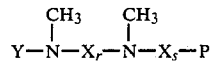

wherein Y is biotin or iminobiotin, X is $CH_2$, P is psoralen or a psoralen derivative, r is an integer equal to or greater than 2 and s is an integer equal to or greater than 1.

The invention also provides a method for preparing a biotinylated psoralen or a biotinylated psoralen derivative.

Further provided are methods for detecting, purifying, and isolating nucleic acids, and methods for delivering an iminobiotinylated psoralen to a cell.

2 Claims, 4 Drawing Sheets

DETECTION OF BIOTINYLATION BY ELISA

BIOTINYLATED PSORALENS

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

Psoralen is a linear three ring heterocyclic compound having the structure

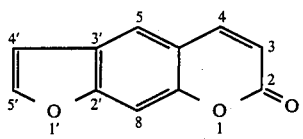

It is a bifunctional photoreactive molecule which forms covalent bonds with nucleic acids in the presence of near ultraviolet (UV) light (1). For a review of psoralen photochemistry, see Hearst (2).

Psoralen's ability to react with DNA has given it clinical importance in the treatment of psoriasis and other skin disorders. Additionally, its ability to form interstrand crosslinks in double stranded DNA has made it a useful reagent in the study of nucleic acid structure and function. Biotin, a growth factor present in very minute amounts in every living cell and occurring mainly bound to proteins or polypeptides, has the structure

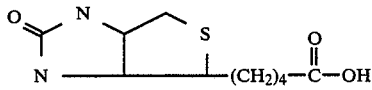

Avidin is a glycoprotein containing four essentially identical subunits, each of which is a single polypeptide chain of 128 amino acid residues with a carbohydrate moiety attached at position 17 (3).

Biotin combines with avidin and becomes inactive (4, 5). The exceptionally high affinity of avidin for biotin has provided the basis for the development of sensitive and specific detection systems. Typically, in a multistep procedure, antigens are recognized by specific antibodies, which are then bound to a biotinylated anti-immunogloulin. This then forms a tight complex with avidin, either conjugated directly to a signal of some kind, such as a fluorescent dye or enzyme, or in turn bound to a biotinylated label. Alternatively, molecules that are themselves directly biotinylated can be recognized directly by avidin, omitting the antibody reactions, with their somewhat lower affinities.

In 1985, G. D. Cimino et al. (6) described the synthesis of a psoralen derivative (aminomethyltrioxsalen-AMT) which contains a biotin moiety attached to the 4' position by various undisclosed linker chains. However, the purported methods for synthesizing these compounds were not disclosed. Furthermore, Cimino et al. reported only that preliminary studies of these undisclosed compunds indicated that they could be used to interchalate and crosslink double-stranded nucleic acid and that they can be detected colorimetrically or fluorescently by standard methods based on the avidin-biotin interaction.

Presently, biotinylated psoralens which retain the biological activity of psoralen and the binding specificity of biotin for avidin are not known. Furthermore, methods for synthesizing compounds which retain the biological activity of psoralen and the binding specificity of biotin are not known. A quick, easy, efficient, and safe method for preparing a biotinylated psoralen would provide readily accessible amounts of biotinylated psoralens useful for psoralen modification of cellular components, the visualization of minute amounts of DNA, investigations of the uptake and distribution of psoralen within cells, the delivery of psoralen to specific cells, and the conversion of nucleic acid molecules to ligands for avidin.

SUMMARY OF THE INVENTION

The present invention provides a compound having the formula

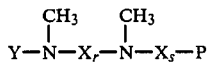

wherein Y is biotin or iminobiotin, X is $CH_2$, P is psoralen or a psoralen derivative, r is an integer equal to or greater than 2 and s is an integer equal to or greater than 1.

The invention also provides a method for preparing a biotinylated psoralen derivative which comprises treating a compound having the structure

wherein L is chlorine, bromine, or iodine and P is psoralen or a psoralen derivative linked to L by $CH_2$ at the 4' position of P with a positively charge multi-aminated linker having two amine groups separated by at least two carbon atoms under suitable conditions so as to allow the formation of a psoralen-linker complex. The psoralen-linker complex is treated with the N-hydroxy succinimide ester of either biotin or iminobiotin under suitable conditions so as to allow the formation of a psoralen-linker-biotin or -iminobiotin complex.

Also provided is a method for delivering to a cell an iminobiotinylated psoralen. This method comprises binding a suitable carrier molecule to biotin so as to form a biotinylated carrier. The biotinylated carrier is bound to avidin so as to form an avidin-biotinylated carrier complex, which is then reversibly bound to an iminobiotinylated psoralen so as to form an iminobiotinylated psoralen-avidin-biotinylated carrier complex. Cells are treated with a suitable amount of the iminobiotinylated psoralen-avidin-biotinylated carrier complex under suitable conditions so as to permit the iminobiotinylated psoralen-avidin-biotinylated carrier complex to become internalized. The treated cells are incubated in the dark under suitable conditions so as to permit the iminobiotinylated psoralen moiety to dissociate from avidin and intercalate into a nucleic acid. The incubated cells are then irradiated with near ultraviolet light under suitable conditions to allow the intercalated iminobiotinylated psoralen to covalently bind to the nucleic acid into which it has intercalated, thereby delivering to the cell an iminobiotinylated psoralen.

The invention additionally provides a method for detecting the presence of a nucleic acid in a sample. This method comprises contacting the sample under suitable conditions in the dark with a biotinylated psoralen so as to allow the biotinylated psoralen to intercalate into a nucleic acid. The sample is then irradiated with near ultraviolet light to permit the intercalated biotinylated psoralen to covalently bind the nucleic acid into which is has intercalated. The biotinylated psoralen which is covalently bound to the nucleic acid is contacted with a detectably marked avidin under suitable conditions so as to allow the avidin moiety to bind to the biotinylated psoralen which is covalently bound to the nucleic acid. The presence of avidin bound to the biotinylated psoralen, which is also covalenty bound to the nucleic acid, is detected and thereby the presence of the nucleic acid in the sample is detected. Furthermore the amount of a nucleic acid in a sample may be quantitatively determined by contacting the biotinylated psoralen which is covalently bound to the nucleic acid with a known amount of a detectably marked avidin. By determining the amount of avidin bound to the biotinylated psoralen which is also covalently bound to the nucleic acid, the amount of the nucleic acid in the sample is also determined.

The invention also provides a method for purifying or isolating nucleic acid from a sample. This method comprises contacting the sample under suitable conditions in the dark with a biotinylated psoralen so as to allow the biotinylated psoralen to intercalate into a nucleic acid. The sample is irradiated with near ultraviolet light to permit the intercalated biotinylated psoralen to covalently bind the nucleic acid into which it has intercalated. The biotinylated psoralen, which is covalently bound to the nucleic acid, is then contacted with an immobilized avidin under suitable conditions so as to allow the avidin moiety to bind to the biotinylated psoralen and form an avidin-biotinylated psoralen-nucleic acid complex. The nucleic acid may then be recovered from the avidin-biotinylated psoralen-nucleic acid complex.

Additionally the invention provides a method for total nucleic acid pattern visualization of a sample. This method comprises electrophoresing the nucleic acid of the sample and immobilizing it to a solid support. The immobilized nucleic acid is contacted with a biotinylated psoralen and the solid support is incubated in the dark for an appropriate amount of time so as to allow the biotinylated psoralen to intercalate into a nucleic acid. Non-intercalated biotinylated psoralen is removed from the solid support and nucleic acid complexes bound to the solid support and intercalated with biotinylated psoralen are irradiated with near ultraviolet light to permit the intercalated biotinylated psoralen to covalently bind the nucleic acid into which it has intercalated. The solid support is contacted with a detectably marked avidin under suitable conditions so as to allow the avidin moiety to bind the biotinylated psoralen, which is covalently bound to the nucleic acid. The presence of avidin bound to the biotinylated psoralen is detected and thereby the total nucleic acid pattern of the sample is visualized.

Furthermore the invention provides a method for visualizing a specific nucleic acid in a sample. This method comprises electrophoresing the nucleic acid of the sample and immobilizing the electrophoresed nucleic acid to a solid support. The immobilized nucleic acid is denatured so as to produced single stranded nucleic acids. Separately, a single stranded nucleic acid clone of the specific nucleic acid to be visualized is contacted with a biotinylated psoralen. The nucleic acid clone is incubated under suitable conditions in the dark so as to allow the formation of biotinylated psoralen-nucleic acid clone complexes, which are then irradiated with near ultraviolet light so as to permit the biotinylated psoralen to covalently bind the nucleic acid clone into which it has intercalated. The immobilized single stranded nucleic acids are contacted with the nucleic acid clone which is covalently bound to the biotinylated psoralen so as to allow the nucleic acid clone and the immobilized single stranded nucleic acids to hybridize. Excess nucleic acid clone which is covalently bound to the biotinylated psoralen is washed from the solid support and the biotinylated psoralen covalently bound to the hybridized nucleic acids is contacted with a detectably marked avidin under suitable conditions to allow the avidin moiety to bind to the biotinylated psoralen which is covalently bound to the hybridized nucleic acids. The presence of avidin-biotinylated psoralen bound to the hybridized nucleic acid molecules is detected and thereby a specific nucleic acid present in the sample is detected.

DETAILED DESCRIPTION OF THE INVENTION

Figure 1:
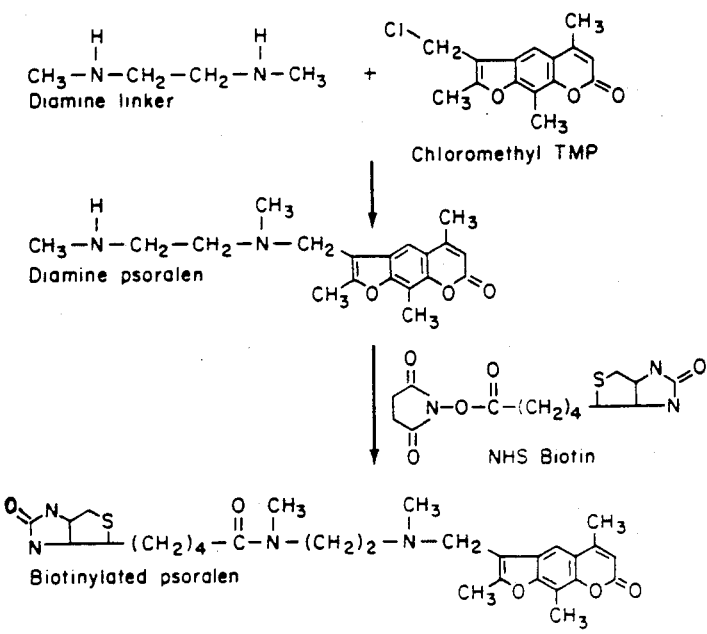
FIG. 1. Synthesis of biotinylated psoralen.

The present invention provides a compound having the formula

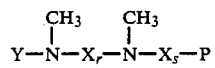

wherein Y is biotin or iminobiotin, X is $CH_2$, P is psoralen or a psoralen derivative, r is an integer equal to or greater than 2 and s is an integer equal to or greater than 1.

In one embodiment of the invention, X is bound to the 4' position of psoralen or a psoralen derivative. The psoralen derivative may be 4, 5', 8 - trimethylpsoralen or 8 - methoxypsoralen.

In another embodiment of the invention r is the integer 2 and s is the integer 1.

The invention also provides a method for preparing a biotinylated psoralen or a biotinylated psoralen derivative which comprises treating a compound having the structure

wherein L is chlorine, bromine, or iodine and P is psoralen or a psoralen derivative linked to L by $CH_2$ at the 4'position of P
with a positively charge multi-aminated linker having two amine groups separated by at least two carbon atoms under suitable conditions so as to allow the formation of a psoralen-linker complex. The psoralen-linker complex is treated with the N-hydroxy succinimide ester of either biotin or iminobiotin under suitable conditions so as to allow the formation of a psoralen-linker-biotin or -iminobiotin complex.

Also provided is a method for delivering to a cell an iminobiotinylated psoralen. This method comprises binding a suitable carrier molecule, i.e. a molecule which is capable of cellular internalization by receptor mediated endocytosis, to biotin so as to form a biotinylated carrier. The biotinylated carrier is bound to avidin so as to form an avidin-biotinylated carrier complex, which is then reversibly bound to an iminobiotinylated psoralen so as to form an iminobiotinylated psoralen-avidin-biotinylated carrier complex. Cells are treated with a suitable amount of the iminobiotinylated psoralen-avidin-biotinylated carrier complex under suitable conditions so as to permit the iminobiotinylated psoralen-avidin-biotinylated carrier complex to become internalized. The treated cells are incubated in the dark under suitable conditions so as to permit the iminobiotinylated psoralen moiety to dissociate from avidin and intercalate into a nucleic acid. The incubated cells are then irradiated with near ultraviolet light under suitable conditions to allow the intercalated iminobiotinylated psoralen to covalently bind to the nucleic acid into which it has intercalated, thereby delivering to the cell an iminobiotinylated psoralen.

Within this application "suitable carrier molecule" includes but is not limited to, insulin and transferrin.

The invention additionally provides a method for detecting the presence of a nucleic acid in a sample. This method comprises contacting the sample under suitable conditions in the dark with a biotinylated psoralen so as to allow the biotinylated psoralen to intercalate into a nucleic acid. The sample is then irradiated with near ultraviolet light to permit the intercalated biotinylated psoralen to covalently bind the nucleic acid into which is has intercalated. The biotinylated psoralen which is covalently bound to the nucleic acid is contacted with a detectally marked avidin under suitable conditions so as to allow the avidin moiety to bind to the biotinylated psoralen which is covalently bound to the nucleic acid. The presence of avidin bound to the biotinylated psoralen, which is also covalenty bound to the nucleic acid, is detected and thereby the presence of the nucleic acid in the sample is detected.

The nucleic acid may be DNA or RNA. Furthermore the amount of a nucleic acid in a sample may be quantitatively determined by contacting the biotinylated psoralen which is covalently bound to the nucleic acid with a known amount of a detectably marked avidin. By determining the amount of avidin bound to the biotinylated psoralen which is also covalently bound to the nucleic acid, the amount of the nucleic acid in the sample is also determined.

The invention also provides a method for purifying or isolating nucleic acid from a sample. This method comprises contacting the sample under suitable conditions in the dark with a biotinylated psoralen so as to allow the biotinylated psoralen to intercalate into a nucleic acid. The sample is irradiated with near ultraviolet light to permit the intercalated biotinylated psoralen to covalently bind the nucleic acid into which it has intercalated. The biotinylated psoralen, which is covalently bound to the nucleic acid, is then contacted with an immobilized avidin under suitable conditions so as to allow the avidin moiety to bind to the biotinylated psoralen and form an avidin-biotinylated psoralen-nucleic acid complex. The nucleic acid may then be recovered from the avidin-biotinylated psoralen-nucleic acid complex.

Additionally the invention provides a method for total nucleic acid pattern visualization of a sample. This method comprises electrophoresing the nucleic acid of the sample and immobilizing it to a solid support. The immobilized nucleic acid is contacted with a biotinylated psoralen and the solid support is incubated in the dark for an appropriate amount of time so as to allow the biotinylated psoralen to intercalate into a nucleic acid. Non-intercalated biotinylated psoralen is removed from the solid support and nucleic acid complexes bound to the solid support and intercalated with biotinylated psoralen are irradiated with near ultraviolet light to permit the intercalated biotinylated psoralen to covalently bind the nucleic acid into which it has intercalated. The solid support is contacted with a detectably marked avidin under suitable conditions so as to allow the avidin moiety to bind the biotinylated psoralen, which is covalently bound to the nucleic acid. The presence of avidin bound to the biotinylated psoralen is detected and thereby the total nucleic acid pattern of the sample is visualized.

Furthermore the invention provides a method for visualizing a specific nucleic acid in a sample. This method comprises electrophoresing the nucleic acid of the sample and immobilizing the electrophoresed nucleic acid to a solid support. The immobilized nucleic acid is denatured so as to produced single stranded nucleic acids. Separately, a single stranded nucleic acid clone of the specific nucleic acid to be visualized is contacted with a biotinylated psoralen. The nucleic acid clone is incubated under suitable conditions in the dark so as to allow the formation of biotinylated psoralen-nucleic acid clone complexes, which are then irradiated with near ultraviolet light so as to permit the biotinylated psoralen to covalently bind the nucleic acid clone into which it has intercalated. The immobilized single stranded nucleic acids are contacted with the nucleic acid clone which is covalently bound to the biotinylated psoralen so as to allow the nucleic acid clone and the immobilized single stranded nucleic acids to hybridize. Excess nucleic acid clone which is covalently bound to the biotinylated psoralen is washed from the solid support and the biotinylated psoralen covalently bound to the hybridized nucleic acids is contacted with a detectably marked avidin under suitable conditions to allow the avidin moiety to bind to the biotinylated psoralen which is covalently bound to the hybridized nucleic acids. The presence of avidin-biotinylated psoralen bound to the hybridized nucleic acid molecules is detected and thereby a specific nucleic acid present in the sample is detected.

The invention also provides a cross-linked double stranded nucleic acid represented by the structure

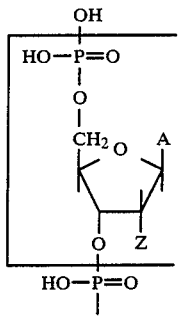 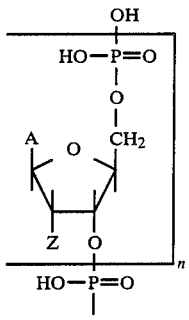

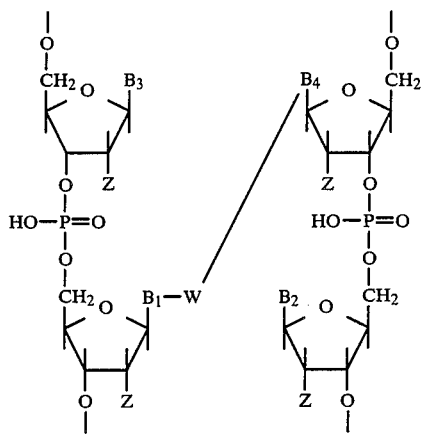

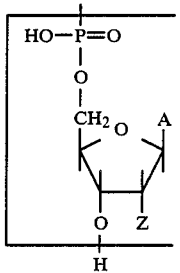 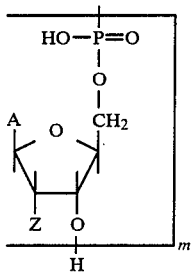

wherein A is a purine or a pyrimidine, $B_2$ and $B_3$ are purines, $B_1$ and $B_4$ are pyrimdines, W is a biotinylated psoralen cross-linked to $B_1$ and $B_4$ such that the 3, 4 and 4', 5' double bonds of W react with the 5, 6 double bonds of $B_1$ and $B_4$ to form cyclobutane products, Z is H or OH and m and n are integers from 0 to about 100,000.

Also provided is a single stranded nucleic acid represented by the structure

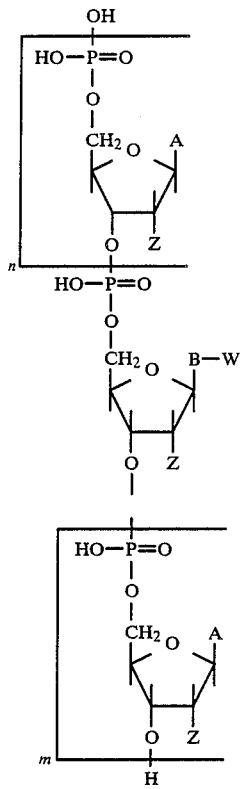

wherein A is a purine or a pyrimidine, B is a pyrimidine, W is a biotinylated psoralen linked to B such that either the 3, 4 or the 4', 5' double bond of W reacts with the 5, 6 double bond of B to form a cyclobutane product, Z is H or OH, and m and n are integers from 0 to 100,000.

The invention further provides a method for detecting in a sample a biotinylated substance. This method comprises contacting a cross-linked double stranded nucleic acid of the present invention with avidin under suitable conditions to allow the avidin to bind to the biotinylated psoralen moiety and form an avidin-biotinylated psoralen-nucleic acid complex. The sample is contacted with the avidin-biotinylated psoralen-nucleic acid complex under suitable conditions to allow the formation of a biotinylated substance-avidin-biotinylated psoralen-nucleic acid complex, the nucleic acid moiety of which is detected, thereby detecting the presence of the biotinylated substances.

The biotinylated substance which is detected may be a biotinylated molecule, cell component, or intact cell. Furthermore, the nucleic acid moiety may be detected by a colorimetric, chemical, or radioactive technique.

A method for detecting in a sample an avidinylated substance is also provided by the present invention. This method comprises contacting the sample with a cross-linked double stranded nucleic acid molecule of the present invention under suitable conditions to allow the formation of avidinylated substance-biotinylated psoralen-nucleic acid complexes. The presence of the nucleic acid moiety of the complexes is detected, thereby detecting the presence of the avidinylated substance.

The avidinylated substance may be an avidinylated molecule, cell component, or intact cell. Additionally, the nucleic acid moiety may be detected by a colorimeteric, chemical, or radioactive technique.

Materials and Methods

Synthesis of Biotinylated Psoralen

Diaminepsoralen (DAPS) was prepared from chloromethyltrimethylpsoralen and sym-dimethylethylene diamine (Aldrich) as described by Welsh (7). Twelve mg of DAPS were dissolved in 0.4 ml dimethylformamide and 15 mg of NHS biotin (Pierce) was added as a solid. The reaction proceeded at room temperature. Reaction progress was followed by thin layer chromatography (TLC) on silica in $CH_2CH_2:NH_3$ saturated methanol (15:1). The $R_f$'s of DAPS, NHS biotin, and the reaction product were 0.25, 0 and 0.28 respectively. After one hour the reaction was complete and the solvent was rotoevaporated off, leaving a yellow oil. All steps were carried out under subdued light, and vessels were covered with aluminum foil when possible.

The product was purified by flash chromatography on a 30×2.5 cm column of silica gel in the TLC solvent system $CH_2Cl_2$ $NH_3$ saturated methanol (15:1). reaction mixture did not dissolve directly in the running solvent, so the yellow oil was first taken up in 0.1 ml $CH_3OH$, and then 1.5 ml $CH_2Cl_2$ was added to the solution. Fractions of about 10 ml were collected by hand and analyzed by TLC. Fractions 15-22 contained the reaction product, running as a single spot with blue fluorescence at $R_f-0.28$. Fractions 17-20 were pooled, dried down, taken up in running solvent as before, and re-chromatographed.

The flash column fractions were analyzed by high pressure liquid chromatography (HPLC) on a reverse phase column, in $CH_3CN$: 0.05 M $NH_4OAc$ (42.5:57.5). Aliquots of the fractions were dried down and dissolved in $CH_3CN$. Each fraction ran as a single sharp peak with a retention time of 5.5 minutes. In this system DAPS and NHS biotin have retention times of 6.2 and 4.1 minutes respectively.

[$^3$H] labelled biotinylated psoralen was prepared from diaminepsoralen and [$^3$H] NHS biotin (Amersham), and purified by preparative HPLC. The specific activity was $3.8 \times 10^{11}$ cpm/mmol

DNA Crosslinking

Plasmid pBR322 DNA was linearized with HindIII, and the DNA purified by phenol extraction, followed by ethanol precipitation and resuspension in 10 mM Tris HCl, 1 mM EDTA, pH 8.0 (TE) at 0.1 mg/ml. Two micrograms of linear plasmid was mixed with 0 to 10 microliters of 5.7 micromolar biotinylated psoralen (BPsor) in a total volume of 12 microliters. The samples were irradiated with near UV light, 340-380 nm, then alkali denatured and run on a non-denaturing 1% agarose gel in the Tris acetate-EDTA, as described in (8).

Detection of DNA modification by ELISA

Calf thymus DNA, at a concentration of 20 micrograms/ml (30 mM base pairs) was combined with 6 uM [$^3$H] BPsor in TE buffer. The sample was irradiated with near UV light, then phenol extracted and ethanol precipitated to remove unbound psoralen. The pellet was resuspended in phosphate buffered saline (PBS). The level of BPsor addition was 0.9%, or 1 psoralen/110 base pairs.

Control DNA samples were prepared by omitting BPsor. Unirradiated controls, prepared by incubating DNA with [$^3$H] BPsor in the dark, followed by phenol extraction and ethanol precipitation, did not incorporate any [$^3$H] BPsor. Microtiter plates were coated with the reacted DNA by adding samples, diluted into PBS, to the wells and drying the plates overnight in a warm room.

The plates were washed three (3) times with 1X PBS-0.5% Tween 20, and 200 microliters of 1% fetal calf serum in PBS-Tween was added to block the wells. After one hour at 37° C. the solution was shaken off. 100 microliters of 5 microgram/ml streptavidin (Bethesda Research Labs-BRL) was added per well, followed by one hour incubation at 37° C. The plates were washed three (3) times with PBS-Tween, and 100 microliters of 1 micrograms/ml biotinylated poly-alkaline phosphatase (BRL) was added, followed by a further incubation of one hour at 37° C. The plates were washed with PBS-Tween, then with 0.01M diethanolamine, pH 8.6. 100 microliters of alkaline phosphatase substrate (Sigma 04), in 1.0M diethanolamine, pH 8.6, was added, and the plates were read at 405 nm after incubation at 7° C.

Lymphocyte proliferation assay

Lymphocytes were isolated from 50 ml of whole blood by centrifugation on Ficoll Hypaque. They were washed twice in Roswell Park Memorial Institute (RPMI) medium, then resuspended in PBS and adjusted to $10^6$ cells/ml in PBS.

BPsor, in ethanol, was added to 4 ml of cells to a final concentration of 1 to 1000 ng/ml. The final ethanol concentration was 1%. Negative controls contained no drug, while positive controls contained 10 ng/ml AMT, in ethanol. After 20 minutes for drug uptake, 200 microliters of the cell suspension was added to wells in microtiter plates. Two dishes were prepared, each with 10 wells of each drug concentration. One was wrapped in aluminum foil and the second was irradiated with 3 J/cm$^2$ of near UV light. The microtiter plates were centrifuged at 1200 rpm for seven minutes, then quickly inverted to discard the PBS. The lymphocytes in the wells were resuspended in 100 microliters RPMI, then half the wells received 100 microliters RPMI-20% fetal calf serum, while the other half received 100 microliters RPMI-20% fetal calf serum-2% PHA. The dishes were incubated for three days at 37° C.

Lymphocyte proliferation was measured by adding [$^3$H] thymidine to each well on the third morning. After six hours the cells were collected with an automatic harvester onto filter paper and washed with 5% trichloroacetic acid (TCA) and ethanol. The filters were counted in a scintillation counter and the stimulation index was calculated as the ratio of [$^3$H]incorporation +PHA/ incorporation −PHA.

Results

Synthesis of biotinylated psoralen

The biotinylated psoralen molecule (BPsor) consists of a psoralen moiety, connected to biotin by a positively charged linker. The linker confers good water solubility to the relatively insoluble psoralen moiety, and the positive charges aid in binding to negatively charged nucleic acids.

The synthesis scheme is outlined in FIG. 1. Chloromethyl trimethylpsoralen was reacted with a diamine linker to form diaminepsoralen. The reaction product was purified and a slight excess of the N-hydroxy succinimide ester of biotin was added. The product of this reaction is BPsor. It was isolated by flash chromatography on silica gel, and the purity was checked by HPLC on a reversed phase column.

DNA Crosslinking

Figure 2:
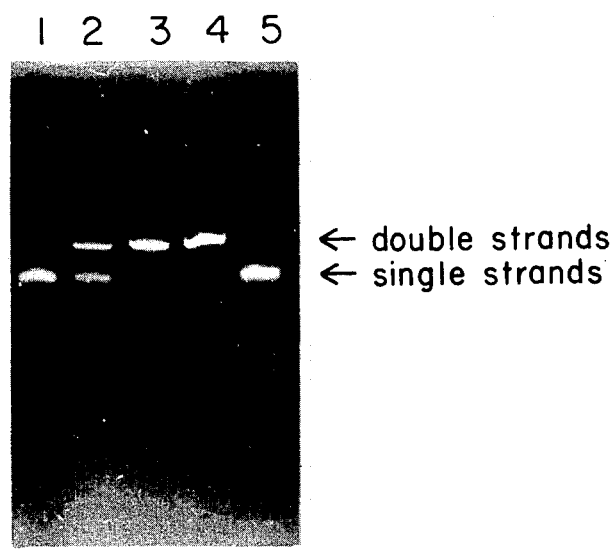
FIG. 2. DNA crosslinking by BPsor. Linear pBR322 DNA (0.2 micrograms) was near UV irradiated in the presence BPsor. Lane 1: no psoralen, lane 2: 6 ng, lane 3: 15 ng, lane 4: 30 ng, lane 5: 30 ng psoralen, but no irradiation.

Psoralens intercalate into DNA in the dark and form covalent bonds at their 3, 4 and 4', 5' double bonds with pyrimidines upon near UV irradiation. If both ends of psoralen are reacted, the result is an interstrand DNA crosslink. The ability of the BPsor to form DNA crosslinks was tested by reacting linear double strand plasmid DNA with this derivative and near UV light. The DNA was then alkali denatured and loaded onto a nondenaturing agarose gel. Crosslinked DNA immediately renatures in the gel buffer and runs as the double stranded form, while non-crosslinked DNA remains single stranded and runs with greater mobility. Increasing amounts of BPsor resulted in increased levels of crosslinking after UV irradiation, while even the greatest amounts of BPsor produced no crosslinking in the absence of light (FIG. 2).

ELISA detection of bindino to DNA and avidin

Figure 3:
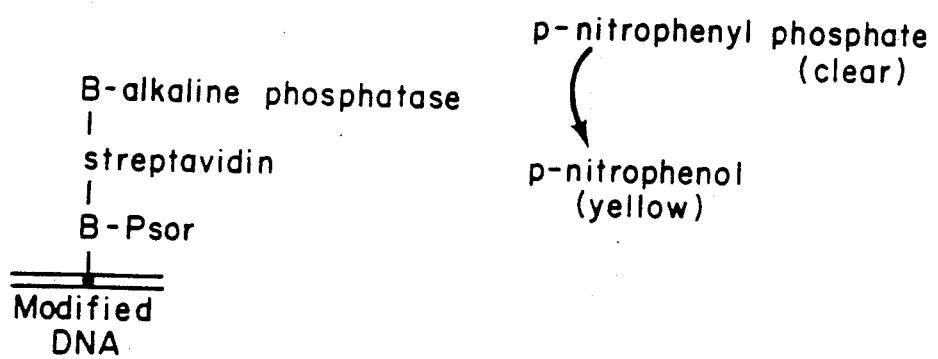
FIG. 3. Detection of BPsor modification of DNA by ELISA. Modified DNA on microtiter dishes was incubated sequentially with streptavidin, biotinylated poly alkaline phosphatase, and phosphatase substrate.

In order to ensure that the linker between the psoralen biotin was long enough to allow access by avidin, the availability of the biotin moiety to avidin binding after the reaction of BPsor with DNA was tested by an enzyme linked immunosorbant assay (ELISA). DNA was reacted with [$^3$H] BPsor plus near UV light and, after the removal of noncovalently bound psoralen by phenol extraction, the modified DNA was bound to microtiter dish wells. After blocking, the samples were incubated first with streptavidin, with has low levels of nonspecific binding to nucleic acids. This step was followed by incubation with biotinylated polyalkaline phosphatase and addition of phosphatase substrate. The steps are outlined in FIG. 3.

The measured enzyme activity was proportional to the added BPsor.

Figure 4:
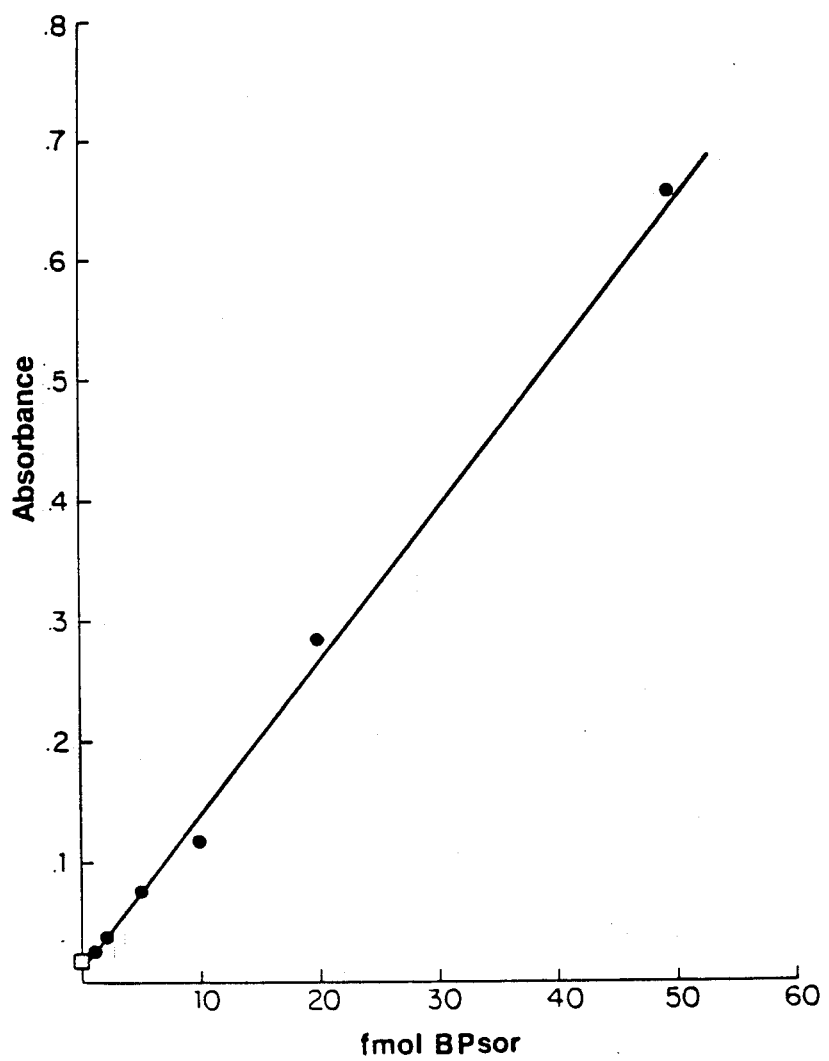
FIG. 4. ELISA of BPsor modified DNA. Alkaline phosphatase activity in samples of DNA reacted with BPsor+near UV light (●) or BPsor alone, without irradiation (□).

After a two hour incubation, alkaline phosphatase reaction at levels two times above background were seen in the wells with 2 fmol of bound BPsor, corresponding to 0.15 ng (FIG. 4). Both BPsor and UV irradiation were required for avidin binding. The control samples, which had been incubated with BPsor but not irradiated, stayed at background levels of alkaline phosphatase activity, as did DNA which had been exposed to light in the absence of BPsor.

These results indicate that both portions of the BPsor are functional. The reagent binds covalently to DNA in the presence of UV light and subsequently binds tightly to avidin.

Inhibition of lymphocyte proliferation

The biological effectiveness of BPsor was tested by assaying its ability to inhibit lymphocyte proliferation. Freshly prepared peripheral blood lymphocytes were incubated with BPsor and exposed to 3 J/cm$^2$ of near UV light. PHA was then added to he treated cells to stimulate their proliferation, and after three days their growth was assayed by measuring [$^3$H] thymidine incorporation. Proliferation is expressed as the stimulation index, the ratio of [$^3$H] incorporation into cells with and without PHA addition.

BPsor addition to lymphocytes at 1 microgram/ml decreased the stimulation index by more than 99% after irradiation, but had no effect in the dark. See Table I below.

TABLE I

| | Inhibition of Lymphocyte Proliferation | |
|---|---|---|
| | Relative Stimulation Index | |
| Treatment | − Light | + Light |
| None | 1.00 | 1.00 |
| 10 ng/ml BPsor | 0.94 | 0.16 |
| 100 ng/ml BPsor | — | 0.01 |
| 1000 ng/ml BPsor | 1.01 | 0.01 |
| 10 ng/ml AMT | 1.02 | 0.02 |

Lower levels of BPsor inhibited growth somewhat less, but even at 10 ng/ml there was an 85% decrease in stimulation. This compares favorably with values of 100 ng/ml for 8MOP, the psoralen derivative in clinical use and AMT, the most active psoralen derivative, at 10 ng/ml.

Discussion

A biotin-containing psoralen derivative (BPsor) has been synthesized from commercially available reagents in a simple two-step reaction, producing a bifunctional nucleic acid- and avidin-binding reagent.

Like other psoralens, BPsor binds covalently to DNA in a near UV photoreaction, resulting in interstrand crosslinks, and like other biotinylated molecules it binds to avidin, even after it has been incorporated into DNA. The biotinylation does not interfere with its biological activity in lymphocytes; treatment with BPsor at 10 ng/ml plus near UV light inhibits PHA stimulation. BPsor shows a potency comparable to that of its immediate precursor, diaminepsoralen, and higher than that of the commonly used psoralen derivative 8-MOP.

The inclusion of a biotin group in psoralen enables the detection of psoralen derivatives with the exquisite sensitivity characteristic of the avidin-biotin interaction. Avidin-biotin systems have been developed with fluorescent, heavy metal, radioactive, immunological, and enzymatic labels. These labels allow measurement in a variety of systems, such as ELISA, filter hybridization, and microscopy of cells and tissue slices of isolated cellular components. Accordingly, BPsor is useful for the following:

(1) Detection of low levels of psoralen addition to cellular components, e.g. by methods such as the ELISA described herein.

(2) Localization of BPsor within cells by microscopy, using fluorescent or enzymatic labels.

(3) Visualization of nucleic acids on filters, gels, or other supports by photoreaction with BPsor, followed by avidin-biotin reactions.

(4) Isolation of psoralen derivatized molecules by affinity chromatography on resins such as avidin-agarose. This reaction can be made reversible by using psoralen derivatized with iminobiotin, which dissociates from avidin at low pH.

(5) Delivery of BPsor to cells as an avidin-BPsor conjugate with a readily internalized molecule, such as transferrin or insulin. A reversible imino-biotin-Psor should be useful for this purpose, as the drug will bind to avidin with a $K_d$ of $5 \times 10^{-7}$ at extracellular pH, but only $10^{-4}$ in the more acidic endosome, leading to dissociation of most of the psoralen. This internalized compound may then be activated by ultraviolet A energy to kill or functionally impair target cells. It is contemplated by the inventors that such a method, used in conjunction with an extracorporeal ultraviolet exposure system such as that described in U.S. Pat. No. 4,321,919 would be useful for the treatment of lymphocytic leukemias and immunologic disorders.

(6) Purification of nucleic acids that hybridize to a probe by crosslinking, denaturing and capturing by avidin affinity. Such a system is advantageous in that it permits an extra denaturation step.

(7) Using DNA molecules to amplify detection of a biotinylated molecule by a DNA based cascade. For example, to amplify an immunoassay, antibody to the antigen to be detected is adsorbed to a microtiter well surface. Following reaction with the antigen specimen, biotinylated antibody against the antigen is complexed. Avidin is then added and further reacted with DNA which has previously been extensively photoderivatized with BPsor. Further amplification is achieved by additional complexing with avidin and a BPsor reacted DNA.

In an extreme version of this method the DNA contains a clonable-selectable gene.

REFERENCES

1. Cole, R. S., Biochem. Biophys. Acta 30–39 (1971).
2. Hearst, J. E., Ann. Rev. Biophys. Bioeng. 10: 69–86 (1981).
3. DeLange, Huang, J. Biol. Chem. 246: 698 (1971).
4. Becker, Wilchek, Biochem. Biophys. Acta 264: 165 (1972).
5. Green, Advan. Protein Chem. 29: 85–133 (1975).
6. Cimino, G. D., Gramper, H. B., Isaacs, S. T., and Hearst, J. E., Ann. Rev. Biochem 54: 1151–1193 (July 8, 1985).
7. Welsh, Ph.D. thesis, Columbia University (1984).
8. Saffran, W. A. Goldenberg, M., Cantor, C. R., Proc. Natl Acad. Sci. USA 79 6594–6598 (1982).

What is claimed is:

1. A compound having the formula

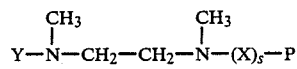

wherein:
P is Psoralen;
Y is biotin or imminobiotin;
X is $CH_2$ and is bound to the 4, position of psoralen; and
s is an integer equal to or greater than 1.

2. A compound having the formula

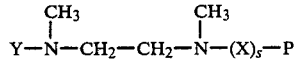

wherein:
P is 4, 5′, 8-trimethylpsoralen or 8-methoxypsoralen;
Y is biotin or imminobiotin;
X is $CH_2$ and is bound to the 4, position of 4, 5′, 8-trimethylpsoralen or 8-methoxypsoralen; and
s is an integer equal to or greater than 1.

* * * * *